(12) United States Patent  
Martin et al.

(10) Patent No.: US 8,448,522 B2
(45) Date of Patent: May 28, 2013

(54) GRIP-MOUNTED SPECIMEN HOLDER

(75) Inventors: Paulo A. Martin, Somerset, MA (US);
James B. Smallwood, Milton, MA (US);
Edward A. McHenry, Jr., Holbrook, MA (US)

(73) Assignee: Illinois Tool Works Inc., Glenview, IL (US)

( * ) Notice: Subject to any disclaimer, the term of this patent is extended or adjusted under 35 U.S.C. 154(b) by 6 days.

(21) Appl. No.: 13/260,989

(22) PCT Filed: Feb. 23, 2010

(86) PCT No.: PCT/US2010/025078
§ 371 (c)(1),
(2), (4) Date: Sep. 29, 2011

(87) PCT Pub. No.: WO2010/114651
PCT Pub. Date: Oct. 7, 2010

(65) Prior Publication Data
US 2012/0024087 A1 Feb. 2, 2012

Related U.S. Application Data

(60) Provisional application No. 61/165,203, filed on Mar. 31, 2009.

(51) Int. Cl.
*G01N 3/02* (2006.01)
(52) U.S. Cl.
USPC .......................................................... 73/856
(58) Field of Classification Search
USPC ................................ 73/864.91, 856; 279/123
See application file for complete search history.

(56) References Cited

U.S. PATENT DOCUMENTS

| | | | |
|---|---|---|---|
| 3,247,565 A | 4/1966 | Griffin | |
| 3,403,549 A | 10/1968 | Griffin | |
| 3,498,121 A | 3/1970 | Engelbrecht et al. | |
| 4,537,080 A | 8/1985 | Christiansen | |
| 5,512,727 A | 4/1996 | Myers et al. | |
| 5,696,328 A | 12/1997 | Underwood et al. | |
| 6,301,972 B1 | 10/2001 | Hall et al. | |
| 7,537,218 B2 * | 5/2009 | Wachtler et al. | 279/123 |
| 7,540,201 B1 * | 6/2009 | Hemmerlin | 73/856 |
| 7,793,553 B2 * | 9/2010 | Lindeman | 73/856 |
| 7,827,868 B2 * | 11/2010 | Lindeman | 73/859 |
| 2002/0166387 A1 | 11/2002 | Grote et al. | |

FOREIGN PATENT DOCUMENTS

| | | |
|---|---|---|
| CN | 2430680 | 5/2001 |
| DE | 10124064 A1 | 11/2002 |
| EP | 1642111 A1 | 4/2006 |
| GB | 620183 A | 3/1949 |

OTHER PUBLICATIONS

ISR for PCT/US2010/025078 dated May 3, 2010.

* cited by examiner

*Primary Examiner* — Lisa Caputo
*Assistant Examiner* — Jonathan Dunlap
(74) *Attorney, Agent, or Firm* — Mark W. Croll; Paul F. Donovan

(57) ABSTRACT

The disclosure relates to a specimen holder for a grip used in materials, or similar testing. The user can position a specimen or testing sample within the open jaw, and then remove his or her hands to a safe location before activating the grip to grip the specimen.

18 Claims, 2 Drawing Sheets

GRIP-MOUNTED SPECIMEN HOLDER

BACKGROUND OF THE INVENTION

This application is national phase of PCT/US2010/025078 filed Feb. 23, 2010, and claims priority under 35 U.S.C. §119 (e) of U.S. provisional application serial no. 61/165,203 filed Mar. 31, 2009.

1. Field of the Disclosure

The present disclosure pertains to a specimen holder for tensile or materials testing, which is mounted directly in the grip of the testing device.

2. Description of the Prior Art

In materials testing, the specimen or testing sample is typically gripped and then pulled or compressed in order to measure the material properties of the specimen. The gripping mechanism can be of several types, including the automatic side-action grip, which can be pneumatic or hydraulic. Typically, the user holds the ends of the specimen between the jaws of the grip and then actuates a switch, typically by the user's hand or foot, to cause the jaws to come together and to grip the specimen. The closing of the jaws is often fast and with enough force that, should the user's fingertips be between the jaws, the user can receive a severe pinch injury. This hazard increases as the jaw face opening increases because this allows more space for a user to insert a finger between the jaws. Industry practice with respect to grips with large jaw face openings is to slow the grip closing speed enough to allow sufficient time for the user to withdraw the finger. However, the slowing of the speed of the jaw face slows the productivity of the user.

It can therefore be difficult to place the specimen or testing sample into position accurately, while maintaining both safety and high work volume.

OBJECTS AND SUMMARY OF THE DISCLOSURE

It is therefore an object of the present disclosure to provide a device for materials testing, or similar devices, wherein the specimen or testing sample can be engaged and positioned within a grip by a device with low operating forces, thereby allowing the user to move to a safe distance from the grip before activating the grip.

This and other objects are obtained by providing a spring-loaded device that holds a specimen in position between the jaws of a grip in a materials testing, or similar machine, for the purpose of allowing the user to remove his or her hand from the grip before actuating the grip, while leaving the specimen in position.

The device of the present disclosure provides an apparatus and method by which a user can remotely operate a grip of a material testing, or similar, device without being exposed to the potentially severe pinch hazard from the grip jaw faces.

The device of the present disclosure employs a low-force spring mechanism with sufficient holding force to support the weight of the specimen. Additionally, the device includes an adjustable specimen stop to allow users to more quickly position the test specimen to a fixed location. The user is able to load a rigid specimen into the grips very quickly by simply pushing the specimen into the device until the specimen abuts an adjustable stop. The user can then simply let go of the specimen and it will remain in place while the user remotely actuates the grip.

Furthermore, the design of the holder allows the user to easily open the holder and keep the holder open while inserting a specimen. This is particularly useful when loading flexible specimens that cannot be pushed into the holder.

The hold is mounted on the grip and can be positioned close to the jaw face of the grip, on either side of the jaw face. In cases where the specimen holder must be positioned in the testing side (or gauge side) of the specimen, an optional pneumatic cylinder can be added to allow the specimen holder to automatically open once the grip force on the specimen reaches a certain preset point. This feature prevents any stray forces being induced into the specimen while it is undergoing testing. The same cylinder can then also reset to the holding position when the forces decrease to a preset point.

Finally, once the test is complete, the specimen holder may hold the broken ends of the specimen from falling from the grips.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENTS

Figure 1:
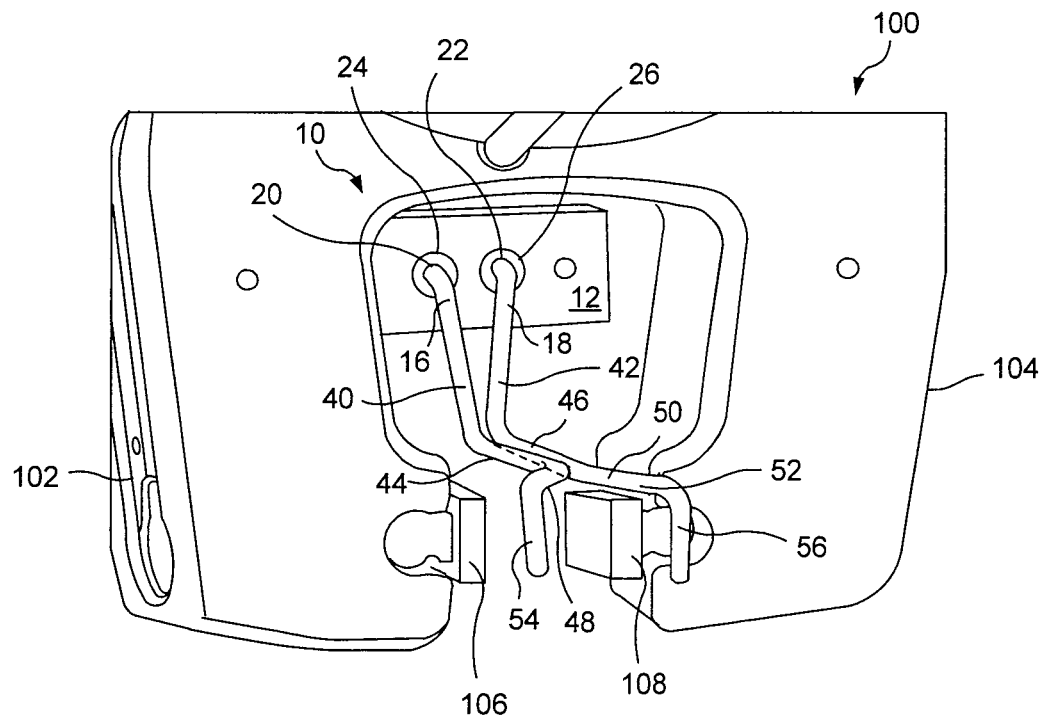
FIG. 1 is a front perspective view of an embodiment of the specimen holder of the present disclosure, shown mounted in a grip.
Figure 2:
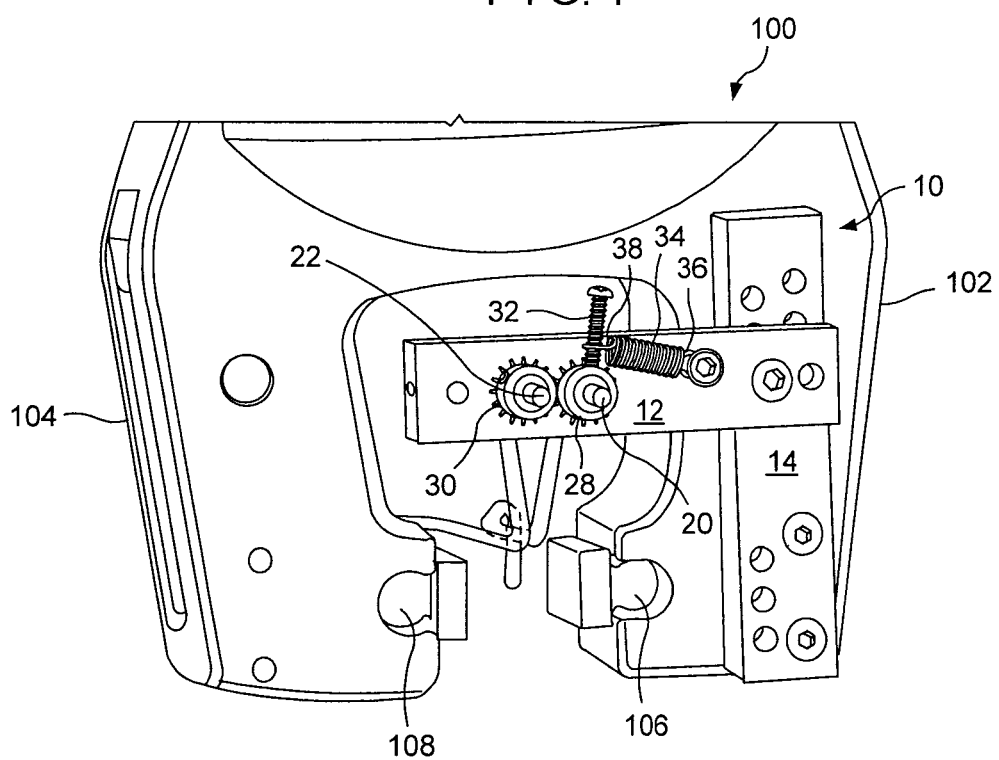
FIG. 2 is a rear perspective view of an embodiment of the specimen holder of the present disclosure, shown mounted in a grip.
Figure 3:
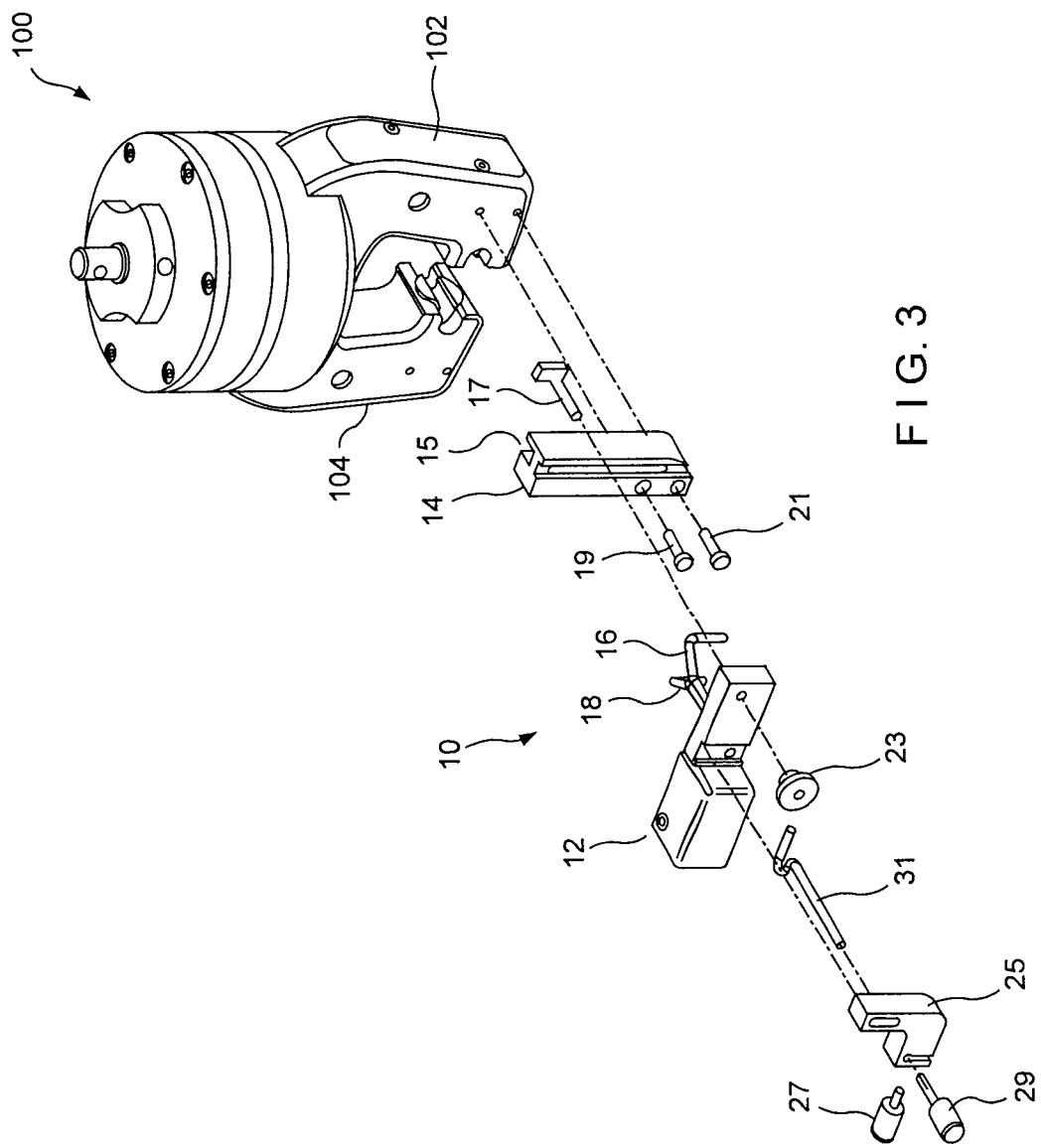
FIG. 3 is an exploded view of a further embodiment of the specimen holder of the present disclosure.

Referring now to the drawings in detail wherein like numerals indicate like elements throughout the several views, one sees that FIGS. 1 and 2 are respective front and rear perspective drawings of the grip 100, including an embodiment the specimen holder 10 of the present disclosure. FIG. 3 discloses a further embodiment of the specimen holder 10.

As is known in the art, the grip 100 includes first and second jaws 102, 104 with respective first and second jaw faces 106, 108. First and second jaw faces 106, 108 reciprocate toward and away from each other, and grip a specimen or testing sample (not shown) therebetween, typically compressing or expanding the sample in a direction parallel to the face of the jaw faces 106, 108.

FIGS. 1 and 2 show that the specimen holder 10 includes a machined plate 12 which is secured to mounting block 14 so as to extend into the space between first and second jaws 102, 104. The combination of the machined plate 12 and the mounting block can be considered to be a mount. As shown in FIG. 3, mounting block 14 may be secured to the rear of grip 100, using conventional mounting hardware such as mounting screws 19, 21. As further shown in FIG. 3, machined plate 12 may be adjustably mounted to mounting block 14 by providing mounting block 14 with slotted passageway 15 through which threaded pin 17 passes and can travel vertically therewithin. Threaded pin 17 further passes through an aperture in machined plate 12 and receives adjusting knob 23. This configuration allows for the adjustment of the vertical position of machined plate 12. Adjustable specimen stop 31 passes through machined plate 12 and is held in by specimen stop block 25. The position of adjustable specimen stop block 25 is adjustable by way of adjusting knobs 27, 29. As will be described herein, the adjustable stop 31 is used to accurately position, or to limit the position of, the specimen or testing sample (not shown) within specimen holder 10.

The specimen holder 10 further includes first and second opposed specimen holding fingers 16, 18, typically formed from bent metal wire or tubular steel or other metal. Those skilled in the art will recognize a wide range of equivalents after review of the present disclosure. The first and second opposed specimen holding fingers 16, 18 include respective first and second axle portions 20, 22 which pass through respective first and second apertures 24, 26 formed in machined plate 12 and are rotationally mounted therein thereby allowing the first and second specimen holding fingers 16, 18 to reciprocate toward and away from each other. Additionally, first and second inter-engaging gears 28, 30 are affixed to respective first and second axle portions 20, 22 immediately to the rear of machined plate 12. First and second inter-engaging gears 28, 30 cause the first and second specimen holding fingers 16, 18 to rotate an equal amount away from and toward the central location of the first and second specimen holding fingers 16, 18 illustrated in FIGS. 1 and 2. Additionally, the affixing of the first and second inter-engaging gears 28, 30 to the respective first and second axle portions 20, 22 longitudinally secures first and second axle portions 20, 22 within respective first and second apertures 24, 26 thereby preventing the removal thereof.

As shown in FIG. 2, first inter-engaging gear 28 includes a radially-extending spring mounting stud 32. Spring 34 includes a first end 36 secured to the machined plate 12 and a second end 38 secured to spring mounting stud 32. Spring 34 serves to rotationally bias the first and second specimen holding fingers 16, 18 to hold a specimen or testing sample (not shown) therebetween, thereby allowing the user to remove his or her fingers prior to activating the first and second jaw faces 102, 104. The strength of the spring 34 is chosen so as to provide sufficient engaging strength of first and second specimen holding fingers 16, 18 for securing the specimen or testing sample (not shown) while allowing simple manual manipulation by the user and not presenting a physical hazard to the user.

Distal ends of first and second specimen holding fingers 16, 18 further include respective first and second downwardly extending portions 40, 42, generally perpendicular to respective first and second axle portions 20, 22. Respective first and second sample holding portions 44, 46 extend perpendicularly (i.e., horizontally in the orientation illustrated in FIGS. 1 and 2) from first and second downwardly extending portions 40, 42 and generally parallel to first and second axle portions 20, 22. First and second sample holding portions 40, 42 are illustrated engaging each other in FIGS. 1 and 2, as a result of the biasing provided by spring 34. Typically, the specimen or testing sample (not shown) is engaged between first and second sample holding portions 44, 46 with a position buttressed by adjustable speciment stop 31. First and second sample holding portions 44, 46 further include respective first and second outwardly flared portions 48, 50 thereby forming V-shaped lead 52 which allows a user to simple push a specimen or testing sample therebetween, thereby spreading the first and second specimen holding fingers 16, 18 apart by the manual force applied to the specimen or testing sample and positioning the specimen or testing sample between first and second sample holding portions 44, 46. Furthermore, adjustable stop 31 (see FIG. 3) can be positioned above or otherwise adjacent to the first and second specimen holding fingers 16, 18 for aiding in positioning the specimen or testing sample (not shown) by limiting the insertion of the specimen or testing sample. First and second downwardly extending portions 54, 56 extend downwardly from respective first and second outwardly flared portions 48, 50 thereby providing the user with a convenient way of manually rotating the first and second specimen holding fingers 16, 18.

As generally described above, in order to use the specimen holder 10 of the present disclosure, the user typically separates the first and second jaw faces 106, 108, inserts a specimen or testing sample (not shown) between first and second specimen holding fingers 16, 18 so that the specimen or testing sample is held in place. The specimen or testing sample may be inserted so as to abut the adjustable stop 31 thereby positioning the specimen or testing sample. The user then removes his or her fingers and any other extremities safely away from the grip 100 and activates the grip 100 so that first and second jaw faces 106, 108 grip the specimen. Materials testing, such as tensile testing, can then be commenced.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A specimen holder for a grip of a materials testing device to engage a specimen prior to activation of the grip, the specimen holder comprising:
   a mount for securing to the grip;
   first and second opposing specimen holding fingers extending from the mount; and
   a mechanism for biasing the first and second opposing specimen holding fingers toward each other so as to be capable of engaging a specimen therebetween within the grip; and
   wherein the mount includes a mounting block for attachment to the grip and a plate attached thereto, the plate being configured and arranged to extend between jaws of a grip.

2. The specimen holder of claim 1 wherein the first and second opposing specimen holding fingers includes respective first and second axle portions and wherein the plate includes first and second apertures for receiving the respective first and second axle portions.

3. The specimen holder of claim 2 wherein the mechanism for biasing the first and second opposing specimen holding fingers toward each other further constrains a distance of movement of the first specimen holding finger away from a central location to be equal to a distance of movement of the second specimen holding finger away from the central location.

4. The specimen holder of claim 3 wherein the mechanism for biasing includes first and second inter-engaging gears, wherein the first inter-engaging gear is secured to the first axle portion and the second inter-engaging gear is secured to the second axle portion.

5. The specimen holder of claim 4 wherein the mechanism for biasing further includes a spring for biasing the movement of the first and second specimen holding fingers toward each other.

6. The specimen holder of claim 5 wherein the first inter-engaging gear includes a radially extending stud and wherein the spring includes a first end and a second end, wherein the first end is attached to the plate and a second end attached to the radially extending stud.

7. The specimen holder of claim 6 wherein the first and second specimen holding fingers include respective first and second specimen holding portions which are substantially parallel to the respective first and second axle portions.

8. The specimen holder of claim 7 wherein distal ends of the first and second specimen holding fingers include outwardly flaring portions thereby forming a V-configuration to allow a specimen to be inserted therethrough, thereby separating the first and second specimen holding fingers.

9. The specimen holder of claim 1 further including a stop device adjacent to the first and second specimen holding fingers for limiting a position of a specimen engaged between the first and second specimen holding fingers.

10. A grip for materials testing, the grip comprising:
first and second jaw faces for gripping a specimen for testing;
a specimen holder for a grip of a materials testing device to engage a specimen prior to activation of the grip, the specimen holder comprising:
a mount secured to the grip;
first and second opposing specimen holding fingers extending from the mount; and
a mechanism for biasing the first and second opposing specimen holding fingers toward each other so as to be capable of engaging a specimen therebetween within the grip; and
wherein the mount includes a mounting block for attachment to the grip and a plate attached thereto, the plate being configured and arranged to extend between the first and second jaws of the grip.

11. The grip of claim 10 wherein the first and second opposing specimen holding fingers includes respective first and second axle portions and wherein the plate includes first and second apertures for receiving the respective first and second axle portions.

12. The grip of claim 11 wherein the mechanism for biasing the first and second opposing specimen holding fingers toward each other further constrains a distance of movement of the first specimen holding finger away from a central location to be equal to a distance of movement of the second specimen holding finger away from the central location.

13. The grip of claim 12 wherein the mechanism for biasing includes first and second inter-engaging gears, wherein the first inter-engaging gear is secured to the first axle portion and the second inter-engaging gear is secured to the second axle portion.

14. The grip of claim 13 wherein the mechanism for biasing further includes a spring for biasing the movement of the first and second specimen holding fingers toward each other.

15. The grip of claim 14 wherein the first inter-engaging gear includes a radially extending stud and wherein the spring includes a first end and a second end, wherein the first end is attached to the plate and a second end attached to the radially extending stud.

16. The grip of claim 15 wherein the first and second specimen holding fingers include respective first and second specimen holding portions which are substantially parallel to the respective first and second axle portions.

17. The grip of claim 16 wherein distal ends of the first and second specimen holding fingers include outwardly flaring portions thereby forming a V-configuration to allow a specimen to be inserted therethrough, thereby separating the first and second specimen holding fingers.

18. The grip of claim 10 further including a stop device adjacent to the first and second specimen holding fingers for limiting a position of a specimen engaged between the first and second specimen holding fingers.

* * * * *